United States Patent
Suter et al.

(10) Patent No.: US 10,155,941 B2
(45) Date of Patent: Dec. 18, 2018

(54) HIGH THROUGHPUT YEAST TWO-HYBRID SCREENING METHOD AND REAGENT KIT

(71) Applicants: Bernhard Suter, San Francisco, CA (US); Lu Zhang, San Ramon, CA (US)

(72) Inventors: Bernhard Suter, San Francisco, CA (US); Lu Zhang, San Ramon, CA (US)

( * ) Notice: Subject to any disclaimer, the term of this patent is extended or adjusted under 35 U.S.C. 154(b) by 1096 days.

(21) Appl. No.: 13/957,408

(22) Filed: Aug. 1, 2013

(65) Prior Publication Data

US 2014/0038831 A1 Feb. 6, 2014

Related U.S. Application Data

(60) Provisional application No. 61/678,412, filed on Aug. 1, 2012.

(51) Int. Cl.
*C12N 15/10* (2006.01)

(52) U.S. Cl.
CPC ............................... *C12N 15/1055* (2013.01)

(58) Field of Classification Search
None
See application file for complete search history.

(56) References Cited

U.S. PATENT DOCUMENTS

| | | | |
|---|---|---|---|
| 6,187,535 B1 | 2/2001 | LeGrain et al. | |
| 6,562,576 B2 | 5/2003 | Manfredl | |
| 7,291,464 B2 | 11/2007 | Kuo | |
| 7,919,610 B2 | 4/2011 | Serebriiskii et al. | |

OTHER PUBLICATIONS

Yu et al (2011 Nature Methods 8:478-80 supplementary materials).*
Shapero et al (2001 Genomic Research 11:1926-34).*
Conrad et al (1992 Nucleic Acids Research 20:6423-24).*
Nat Methods. Apr. 2013;10(4):339-42. doi: 10.1038/nmeth.2397. Epub Mar. 3, 2013. A Y2H-seq approach defines the human protein methyltransferase interactome. Weimann M, Grossmann A, Woodsmith J, Özkan Z, Birth P, Meierhofer D, Benlasfer N, Valovka T, Timmermann B, Wanker EE, Sauer S, Stelzl U.
Nucleic Acids Res. Feb. 1, 2013;41(3):1496-507. doi: 10.1093/nar/gks1329. Epub Dec. 28, 2012. Development and application of a DNA microarray-based yeast two-hybrid system. Suter B, Fontaine JF, Yildirimman R, Raskó T, Schaefer MH, Rasche A, Porras P, Vázquez-Álvarez BM, Russ J, Rau K, Foulle R, Zenkner M, Saar K, Herwig R, Andrade-Navarro MA, Wanker EE.
Nat Methods. Jun. 2011;8(6):478-80. doi: 10.1038/nmeth.1597. Epub Apr. 24, 2011. Next-generation sequencing to generate interactome datasets. Yu H, Tardivo L, Tam S, Weiner E, Gebreab F, Fan C, Svrzikapa N, Hirozane-Kishikawa T, Rietman E, Yang X, Sahalie J, Salehi-Ashtiani K, Hao T, Cusick ME, Hill DE, Roth FP, Braun P, Vidal M.
BMC Genomics. Jan. 9, 2012;13:8. doi: 10.1186/1471-2164-13-8. Quantitative Interactor Screening with next-generation Sequencing (QIS-Seq) identifies *Arabidopsis thaliana* MLO2 as a target of the Pseudomonas syringae type III effector HopZ2. Lewis JD, Wan J, Ford R, Gong Y, Fung P, Nahal H, Wang PW, Desveaux D, Guttman DS.

* cited by examiner

*Primary Examiner* — Christopher M Gross
(74) *Attorney, Agent, or Firm* — U.S. Fairsky LLP; Yue (Robert) Xu

(57) ABSTRACT

An approach to collect and interpret results from Y2H screens uses high-throughput next-generation sequencing technologies. In particular, this system is appropriate to generate comprehensive profiles of protein-protein interactions (PPIs), allowing also a side-by-side comparison of specific PPI patterns with that from control samples and allows a direct comparison of PPI patterns displayed by proteins in their wild-type and various mutant conformations. While sample preparation relies to the most part on established transcriptome and RNA sequencing procedures, this invention also encloses a specific DNA preparation step to sequester irrelevant and contaminating sequences from the sample.

7 Claims, 8 Drawing Sheets

| Genes | Pos. | p53 | Pool | Ratio log |
|---|---|---|---|---|
| ARHGDIB | 0 | 81575.59 | 3.95 | 4.37 |
| PIAS2 | 1 | 82406.21 | 2.31 | 4.55 |
| PGM1 | 0 | 33393.93 | 1.49 | 4.35 |
| IDO1 | 0 | 29158.59 | 1.29 | 4.35 |
| NPC2 | 0 | 27348.74 | 2.81 | 3.99 |
| UBE2E3 | 0 | 13200.18 | 1.61 | 3.91 |
| CMPK1 | 0 | 9916.03 | 1.36 | 3.86 |
| SF3S5 | 0 | 8060.51 | 0.86 | 3.97 |
| DCAF6 | 0 | 7889.88 | 0.93 | 3.93 |
| MRVI1 | 0 | 7641.79 | 874.18 | 0.94 |
| ATF7IP | 0 | 6338.18 | 0.35 | 4.26 |
| ATP1B3 | 0 | 6158.84 | 2.3 | 3.43 |
| OSBPL1A | 0 | 5418.83 | 0.85 | 3.80 |
| ZKSCAN4 | 0 | 4762.23 | 0.29 | 4.22 |
| ROCK2 | 0 | 3706.88 | 0.1 | 4.57 |
| WDR48 | 1 | 3240.16 | 0.51 | 3.80 |
| ATP1B1 | 0 | 2712.71 | 3.2 | 2.93 |
| ANAPC10 | 0 | 2519.44 | 3.12 | 2.91 |
| TOPORS | 1 | 2213.62 | 0.24 | 3.96 |
| EIF1B | 0 | 2000.46 | 4.25 | 2.67 |
| C14orf45 | 0 | 1977.89 | 6.01 | 2.52 |
| EPCAM | 0 | 1833.61 | 2.65 | 2.84 |
| MTMR6 | 0 | 1636.85 | 0.63 | 3.41 |
| COPS5 | 1 | 1502.43 | 3.98 | 2.58 |

HIGH THROUGHPUT YEAST TWO-HYBRID SCREENING METHOD AND REAGENT KIT

CROSS REFERENCES TO RELATED APPLICATIONS

This application claims the benefit of U.S. Provisional application No. 61/678,412, filed Aug. 1, 2012, which is incorporated herein by reference in its entirety.

FIELD OF THE DISCLOSURE

This invention relates to the field of protein-protein interactions, specifically the Y2H system. The invention also relates to the technical field of next-generation sequencing technologies since it was the method used to assess the systematic and comprehensive analysis of the outcomes of Y2H screens.

BACKGROUND OF THE INVENTION

Protein-protein interactions underlie virtually every process in a living cell, such as signal transduction, cytoskeletal organization, virus-host cell recognition, assembly of multiprotein complexes, and many more. Consequently, the exploration PPIs of entire PPI networks is a formidable goal in systems biology. The establishment of high-confidence PPIs is crucial for the understanding of diseases and can provide the basis for new therapeutic approaches.

Yeast Two-Hybrid (Y2H) is a sensitive and widely applied method to screen for protein-protein interactions (PPIs) and was instrumental in the detection of many biological processes and disease mechanisms (Ratushny and Golemis 2008; Hamdi and Colas 2012). Exploiting the power of yeast genetics, reconstituted PPIs can be selected out of a large number of potential combinations by selective growth of yeast cells. Specifically, reconstituted PPIs drive reporter gene activation, which allows the selection of a few yeast clones that express interacting proteins against a large background of cells with noninteracting proteins. In the conventional scheme of Y2H', a transcription factor is split into its DNA binding and activation domains (DBD and AD)', and functionally reconstituted via the physical interaction of fused bait and prey proteins (FIG. 1). While in the original implementation of the system', the transcription factor was the Gal4 protein', lexA based systems are applied as an alternative (Fields and Song; Paroush, Finley et al. 1994; Golemis, Serebriiskii et al. 2009). The reconstituted transcription factor drives the expression of reporter genes that is scored by growth (typically HIS3 and lacZ). Bait and prey vectors contain promoters that regulate transcription of the fusion genes and marker genes (typically TRP1 and LEU2). Y2H assays hence often use selective medium lacking leucine, tryptophan, and histidine. Selected bait-prey combinations grow as colonies on the selective plates and are identified by DNA sequencing. Using conventional sequencing technology (Sanger sequencing), the identification of the screening results is major limitation for the scale and throughput of Y2H.

In the traditional setup of a cDNA library based Y2H, a specific bait construct of interest is combined with a cDNA library of prey fusions. This conventional procedure applies a rather laborious effort with a considerable amount of consumables and is usually only performed in a single replicate. An important alternative to cDNA based Y2H screens are matrix-based Y2H approaches. In these experiments, annotated and assembled open reading frames (ORFs) in bait and prey strains are combined one-by-one using automated procedures (Uetz, Giot et al. 2000; Stelzl, Worm et al. 2005). Notably, such approaches with preassembled ORF libraries were applied for comprehensive PPI analysis of in eukaryotic model organisms, such as yeast (Uetz, Giot et al. 2000; Ito, Chiba et al. 2001; Giot, Bader et al. 2003; Yu, Braun et al. 2008), and importantly also for a first overview of the human interactome (Rual, Venkatesan et al. 2005; Stelzl, Worm et al. 2005). While such matrix-based systems eliminate the need to do sequencing reactions for the identification of proper bait-prey interactions, their use is restricted to annotated and cloned collections of open reading frames.

Despite their popularity, Y2H interaction screening assays generate false positive results that are caused by artifacts and erroneous reporter gene activation (LaCount, Vignali et al. 2005). Activation of reporter gene transcription in the absence of a functional bait or prey (self- or autoactivation) is common in Y2H screens, and in certain screening setups the backgrounds of unspecific and erroneous results is up to 90%. In conventional library screens, Y2H interactions are usually confirmed by isolation of the interacting prey clone and retransformation into fresh cells, followed by retesting the interaction with fresh original bait and proper controls (Walhout and Vidal 2001). Reporter activation should only be observed with the correct bait-prey combination, while reporter with prey and a control (e.g. empty bait vector, irrelevant protein) displays a false positive or unspecific interaction. False positives that can be addressed this way are also coined as technical false positives that are caused by the inherent properties of the underlying yeast screening system (Vidalain, Boxem et al. 2004). Typically, unspecific activation by preys occurs by a genuine interaction of the prey protein with the DNA binding domain encoded by the bait vector or some component of the yeast transcription machinery. Unspecific activation by baits occurs often when the bait protein is a transcription factor or has some transcription factor-like properties. Notably, false activation (autoactivation) is more frequent with bait (ca. 20%) than with prey proteins (expected ca. 5%). In a conventional screening setup, however, in which individual baits are screened with complex libraries of prey proteins, bait autoactivators provide a lesser problem since they can be tested prior to the screen. On the other hand, the prey libraries are very complex with >3×10$^6$ prey clones/library. Hence the occurrence of false positives in prey cDNA libraries is often very difficult to predict and control, especially when relatively few assays are undertaken.

Four relevant criteria have been established for a proper execution for high-throughput Y2H (Yu, Braun et al. 2008; Simonis, Rual et al. 2009; Venkatesan, Rual et al. 2009). First, the number of physical protein pairs (bait-prey) that are being tested in a given search space (completeness). More specifically, this is the total of all possible combinations between the bait being tested in the screen and the preys that are physically present in the particular cDNA library. The second criterion is assay sensitivity, measuring potential interactions that can and cannot be detected in a particular setup. Assay sensitivity in the Y2H setup can be restricted by the physical inaccessibility of a particular domain for the interaction. Systematic false negatives caused by steric exclusions or domain folding have to be addressed with different bait fragments, or swapping the orientation of the bait fusion construct (Rajagopala, Hughes et al. 2009). The third criterion is sampling sensitivity: the fraction of all detectable interactions found by a single implementation of the assay; and fourth is precision, which is the proportion of true versus false positives detected in the assay.

So far, Y2H results, also those generated in high-throughput experiments are not based on truly quantitative measurements. This contrasts with gene expression and protein-DNA interactions. For this, DNA microarrays were instrumental. The application of this technology vastly increased throughput and quantitative analysis of expression and interaction profiles generated a vast amount of biological insight (Allison, Cui et al. 2006). However, recent years saw the emergence of next-generation sequencing (NGS) technologies becoming dominant methodologies for many applications in genomics and systems biology, replacing DNA microarrays in applications such as transcriptome analysis (RNA-Sequencing), chromatin immunoprecipiation (Chip-Seq), and diverse other assays (Metzker 2005; Johnson, Mortazavi et al. 2007; Morozova and Marra 2008; Fox, Filichkin et al. 2009; Metzker 2010). Importantly, NGS approaches allow an inexpensive production of very large volumes of sequence data. For transcriptome analysis, sequencing of the total cellular RNA content has two major advantages over DNA microarray based analysis: the more precise readout over a larger dynamic range and the possibility to identify novel and previously unannotated transcripts. The most widely used system for NGS is by now the Illumina systems, which was widely used for transcriptome studies by many researchers (Marioni, Mason et al. 2008; Lazarevic, Whiteson et al. 2009; Filichkin, Priest et al. 2010; Levin, Yassour et al. 2010; Alsford, Turner et al. 2011; Zhang, Cheranova et al. 2012).

Lewis and Wan recently reported a global pooling scheme and screening scheme followed by a selective readout by the Illumina next-generation sequencing system (Lewis, Wan et al. 2012). Quantitative Interactor Screen Sequencing (QIS-Seq). This method applied amplification from selected pools of a conventional cDNA prey library. Additionally, it requires transformation of the entire prey library for individual baits. In effect, a new pool is generated for each screen. Because de novo transformation of a library for each individual bait and control is laborious and time consuming, this method is ineffective for commercial purpose. Therefore a method is needed to efficiently analyze the prey library pool. Only with increased analysis efficiency, it will be possible to run the analysis in multiples to obtain statistically increased accuracy.

BRIEF SUMMARY OF THE INVENTION

A method disclosed herein takes advantage of the recent advent of next-generation technologies for applying to a comprehensive and almost limit-free methodology for the analysis of Y2H results, which should greatly enhance the analysis of protein interactomes. An application as described is focused on specific Illumina NGS system, which is well established and widely used for different applications. The invention offers the sequencing of all outcomes from a Y2H screen in a single pool, therefore overcoming the previous limitations in scale and cost when outcomes from Y2H by single sequence reactions. The method is amenable to quantitative statistics and sets of control screens can be used to compare the results from a specific bait screening with results from unspecific and background Y2H activation. Hence, the comprehensive approach, the massive increase in scope for the readout and the sharply reduced costs results not only in an increased sampling and screening sensitivity but also in an enhanced specificity, since 'real' PPIs from the Y2H screen can be more accurately predicted. This invention also applies a special step for the preparation of the selected sequences from the Y2H experiments. Specifically, this method allows the selective enrichment of the cloned cDNA inserts from the plasmid vector sequence, while eliminating all other sequences (vector and contaminating DNA) that would also be identified in a respective sequencing reaction. If vector and other contaminating sequences were not eliminated, a large part of the available sequencing space would be taken up by noninformative sequence reads. The particular purification and enrichment step is beneficial for the commercial application for NGS Y2H and hence an integral part of the entire procedure that is disclosed here.

The methodology that is presented here to specifically enrich and extract cDNAs from vectors can in principle also be applied to any other approach besides Y2H for which the goal lies in the selection of cDNA for a specific purpose. This could be for the exploration of PPIs with methods that are related to the Y2H system, such as protein fragment complementation (PCA), the gene overexpression on a host organism, or any other functional assay in which the expression of a specific cDNA in a vector construct results in a measurable growth effect or any other selectable phenotype. Hence, the enrichment procedure presented here can be understood, in principle, as a 'reverse cloning' procedure with the goal to obtain the selected (or unselected) cDNA population of interest, whose composition was defined by the nature of the applied selection assay, without any contaminating sequences that are related from the selective process (vector or host DNA). The composition of the individual cDNA fragments will be retained as corresponding to the original RNA (or DNA) sequences but flanked with small adaptor sequences that were used for cDNA construction.

We devise here a tailored application to obtain comprehensive and quantitative readouts, rather than a novel Y2H system or a related method, comprising vector and marker constructs. The methodology presented here can be applied to different existing Y2H systems. In some of the embodiments disclosed this application, the invented Y2H procedure and readout is applied to a commercial Clontech Y2H kit (Matchmaker system).

In an embodiment of the invention, a method for determining the DNA sequences of prey proteins that interact with bait protein include (1) conducting a bait screen including the steps of: (a) introducing a library of Y2H prey vectors into a Y2H host strain to produce a library of hybrid Y2H cells, wherein each of the Y2H prey vectors includes a prey fusion construct for expressing a prey fusion protein, and wherein said Y2H host strain includes assay bait fusion construct; (b) growing said hybrid Y2H cells in a selecting condition for a defined time or for a defined cell growth, allowing said Y2H host strain cells to express said prey fusion construct, assay bait fusion construct, and reporter gene construct, wherein cell growth correlates to expression of said reporter gene construct that measures functional reconstitution of assay bait fusion protein and prey fusion protein; (c) PCR amplifying prey ORFs in the prey fusion constructs from said pool of Y2H host strain cells using a flanking set of specific primers, wherein amplification is done under controlled conditions, for example, low cycling numbers, to avoid generation of artifacts and erroneous PCR products; (d) purifying pool of PCR amplified prey ORFs; and (e) analyzing pool of purified PCR amplified prey ORFs using a high throughput DNA sequencing method that reads DNA sequences and gives quantitative information of composition of said pool of purified PCR amplified prey ORFs.

(2) conducting one or more control screens that are parallel to said bait screen described above, i.e. having the same steps, but with one or more differences, including: (a) in lieu of step (1)(a), using a Y2H host strain that includes control bait fusion construct but not assay bait fusion construct, wherein cell growth correlates to expression of said reporter gene construct that measures functional reconstitution of control bait fusion protein and prey fusion protein; (b) in lieu of step (1)(a), using a Y2H host strain that includes no bait fusion construct; or (c) in lieu of step (1)(b), growing said hybrid Y2H cells without a selecting condition; and (3) applying quantitative statistics to determine bait specific positive results.

In some aspects of the embodiment, the library of Y2H prey vectors is included in a pool of haploid yeast cells of a first mating type. The Y2H host strain cells are haploid yeast cells of a second mating type that is capable of mating with the first mating type. By mating the haploid yeast cells including the prey vectors and the Y2H host strain cells, the resulting diploid hybrid Y2H cells are produced in high efficiency.

In some other aspects of the embodiment, multiples of bait screens and control screens may be conducted to obtain discrete sets of scores, and computer operated quantitative statistics is applied to determine bait specific positive results, and to assess relationship between bait mutation and protein-protein interaction. In yet other aspects, in the flanking set of specific primers, at least one of them includes at least one affinity tag.

In another aspect, the affinity tag may be biotin, glutathione, His, Flag, thiol, amino, azido, or acetylene. In a further aspect, the affinity tag is biotin. In yet another aspect, excess primers may be removed by size exclusion methods. The biotinylated PCR product mixture is incubated with streptavidin coated solid support. Unbound DNA and other components in PCR reaction mixture are removed by washing, and the streptavidin coated solid support is treated with restriction enzyme to release prey cDNA inserts. The streptavidin coated solid support may be magnetic bead. The restriction enzyme may be a restriction enzyme that recognizes and cuts at restriction sites that were used for cloning the prey cDNA construct or are otherwise suitable for the separation of the cDNA from the vector sequences. In the flanking set of specific primers, each primer may include at least one affinity tag.

In another embodiment, a method for analyzing a pool of sample DNA fragments includes the steps of (1) applying PCR amplification to the pool of sample DNA fragments, using at least one pair of PCR primers, to obtain a pool of amplified fragments in a PCR reaction mixture, wherein at least one amplified fragment is obtained from each sample DNA fragment, and each amplified fragment includes a length of specific sequence; (2) purifying the pool of amplified fragments from the PCR reaction mixture to obtain a pool of purified fragments; and (3) analyzing the pool of purified fragments using high throughput DNA sequencing method to obtain (a) sequencing information of said length of specific sequence on each amplified fragment, and (b) relative copy numbers of each amplified fragment.

In an aspect of the embodiment, each of the DNA sample fragments is a vector. In another aspect, for each pair of PCR primers, at least one of the primers includes one or more affinity tags. The affinity tag may include a functional group selected from the group consisting of biotin, glutathione, His, Flag, thiol, amino, azido, and acetylene.

In another aspect, the method includes purifying the pool of amplified fragments over a solid support coated with streptavidin, and wherein the affinity tag includes one or more biotin groups. The method may include the steps of (1) binding the pool of amplified fragments to the solid support coated with streptavidin; (2) washing to remove components that are not bound to the solid support; and (3) treating the amplified fragments bound on the solid support with one or more restriction enzymes to obtain a pool of purified fragments, wherein the purified fragments are restriction fragments, wherein the restriction fragments include the length of specific sequences. The solid support coated with streptavidin may be magnetic bead coated with streptavidin. In another aspect, each primer may include a biotin functional group.

In another embodiment of the invention, a kit includes a vector containing a prey fusion construct encoding a prey fusion protein; a vector containing a bait fusion construct encoding a bait fusion protein; a vector containing a reporter gene construct; a Y2H host strain; and a set of PCR primers that flank said prey fusion construct. The kit may further include streptavidin coated solid support, and at least one of the PCR primers may include a biotin label.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
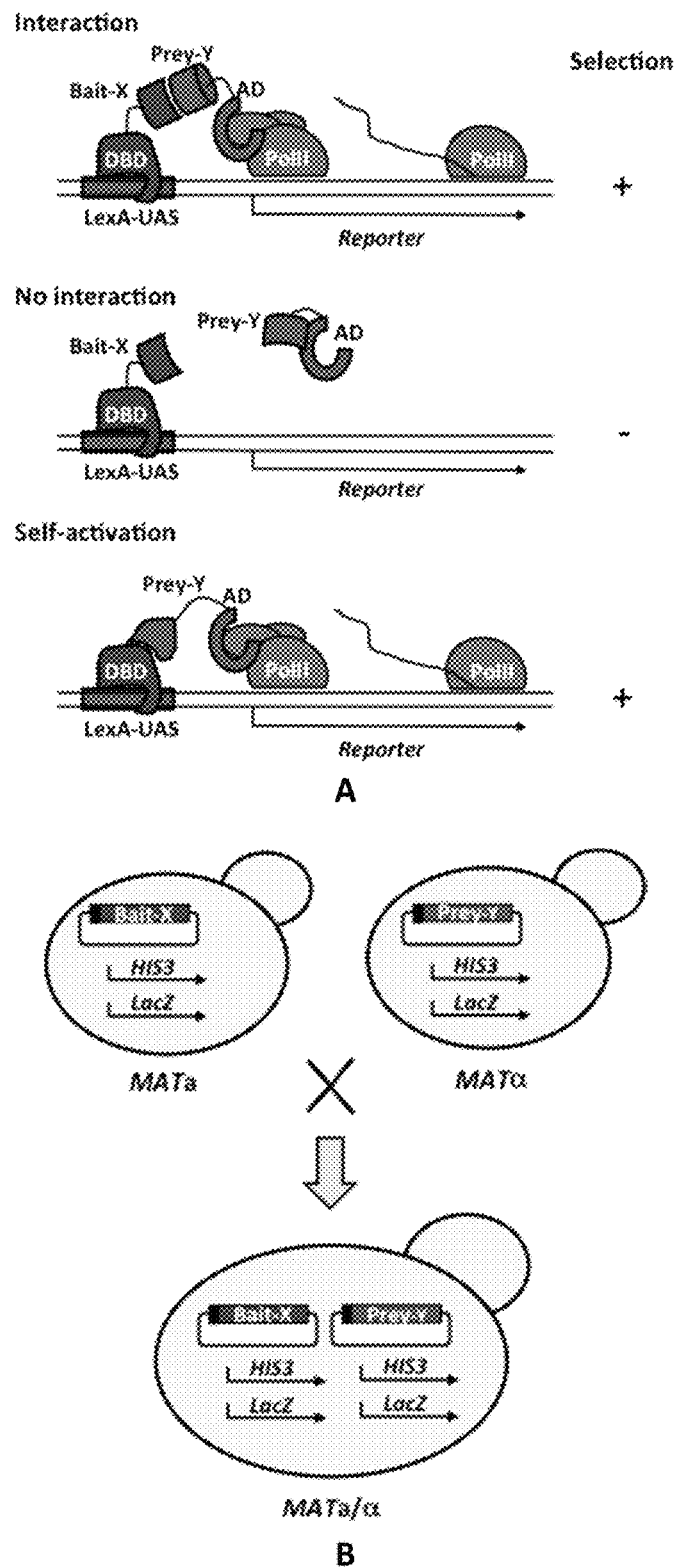
FIG. 1 is a schematic explanation of the Y2H principle. Panel A shows the principle of Y2H interactions and readouts. A split transcription factor (Gal4) consisting of the activation domain (AD) and DNA-binding domains (DBD) is reconstituted via the physical interaction of fused bait and prey proteins. This drives the expression of a gene that results in a growth (HIS3) or coloration phenotype (lacZ). Growth and color phenotypes are scored: activation by correct bait-prey interaction (true positive); no interaction (negative); and nonspecific (self)-activation by bait or prey alone (false positive). (B) Mating and matrix based Y2H. Bait (X) and prey (Y) constructs are combined via mating of Mata (bait strain) and Matα (prey strain) strains. Reporter genes are HIS3 and lacZ. Hybrid yeast cells that express interacting bait and prey proteins activate the transcription of the reporter genes.

that were used to construct the insertion of the cDNAs (white). 2. Pulldown of biotinylated PCR product with streptavidin beads (Dynabeads® kilobase BINDER™ Kit). This step isolates the amplified prey inserts from the residual vector DNA. 3. Prey cDNA inserts are released from the beads by SfiI digestion. This step eliminates the flanking sequences from the prey cDNAs. The fragmentation, end repair and adaptor ligation, multiplexing (steps 4 and 5) are standard procedures in the modified protocol from Illumina for transcriptome analysis that was applied here. (B) Proof-of-principle experiment. The procedure was applied to a normalized human cDNA library that was cloned within SfiIA/B sites in pGADT7-RecAB vector) Prey cDNA was from a p53 screen (p53) and from the nonselected sample (pool), both amplified from pGADT7-RecAB plasmid after plasmid extraction from yeast with primers P1 and P2. P1 and P2 both directed at the MCS in pGADT7-RecAB (P1 forward, P2 reverse). Amplification was done with either a 5'-biotinylated (+BIO) or an unmodified (−BIO) primer pair (1.INPUT). After binding the PCR products to streptavidin beads, the supernatant was checked for unbound DNA (2.SUP). The PCR products on the beads were either digested with SfiI restriction enzyme (+SfiI) or mock-treated (−SfiI). Samples were checked on 1% agarose gels. Amount of input and released DNA was measured with Nanodrop, and the % yield was calculated. (C) The additional purification via pulldown and SfiI digestion does not introduce significant alterations in the composition of the pool of PCR products. Two PCR products were generated from plasmid DNA that was isolated from yeast cells that contain the original pool prey cDNAs (Pool2-2, Pool2-57). Both PCR products were generated with biotinylated (Bio-TEG) primers. Pool2-2 PCR product was subjected to the additional purification step with biotin-binding and SfiI digestion, while Pool2-57 product was directly used for Illumina sample prep without the additional steps. Both samples were run on 1 Illumina MiSeq flow cell (running for short single reads), resulting in ~4.7×10$^5$ reads for Pool2-2 and ~1×10$^6$ reads for Pool 2-57. The reads were aligned to the human genome reference database and converted to fragments per kb per million reads (FKPM) using the Cufflinks-TopHat pipeline. FPKM values mapped to individual transcripts at the gene level were transformed to log 2 scale and compared in the plot (Pool 2-2, X-axis; Pool 2-57, Y-axis). Spearman correlation for the read mappings of several thousand gene fragments was 0.965.

FIG. 4 shows the readout from a next-generation sequencing based Y2H screen using a fragment of the p53 oncogenes as bait with a Matchmaker cDNA library (Clontech). FIG. 4 shows the 25 most enriched genes in the bait screen when compared to the unselected pool. Reads were normalized for average reads per million per kilobase according to (Johnson, Mortazavi et al. 2007). Ratios based on the number of normalized reads that were measured for a specific prey clone (geneID) compared to those measured for the unselected control (original cDNA library or pool).

Figure 5:
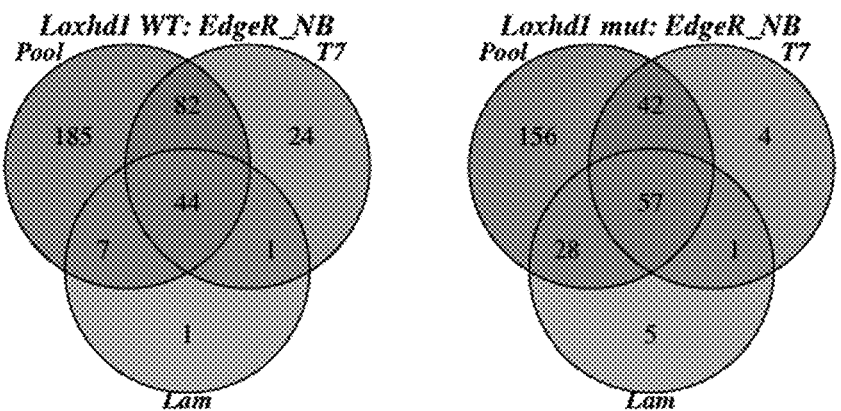
Figure 5:
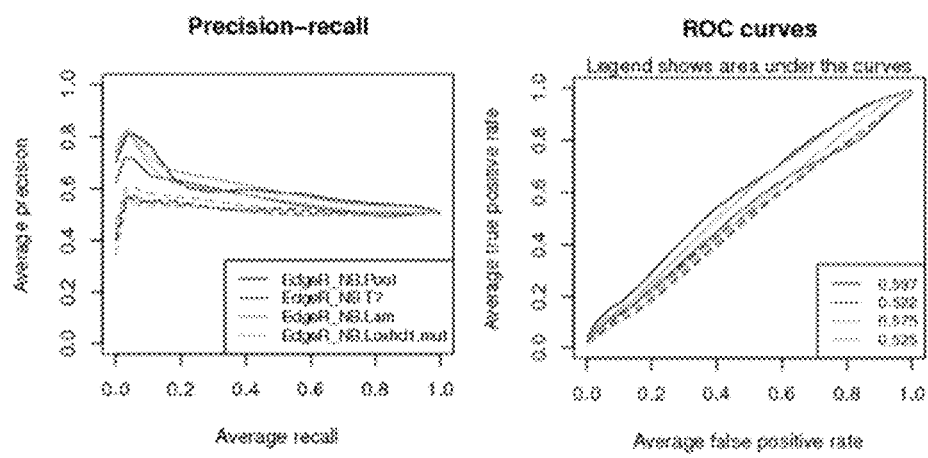

FIG. 5. (A) Venn diagrams for overlapping FC-scores from Loxhd1-WT and Loxhd1-mutant screens via EdgeR-NB analysis with 70$^{th}$ percentile cutoffs. (B) Quantitative benchmarking of log 2-FC (EdgeR-NB) for Loxhd1-WT over pool, T7 and Lam controls, and Loxhd1-samba (mutant) as numerical scores and GO: 0007605 "Sensory perception of sound" as binary classifier. Precision, recall, and ROC are displayed as repeat sampling curves with Qisampler. For ROC, the area under the ROC curve (ROC AUC) is calculated. Sampling curves are shown as closed lines and random sets (no discrimination) as dashed lines. Sampling was performed in 100 repetitions, with a rate of 0.5 (100% of classifiers sampled per run).

Figure 6:
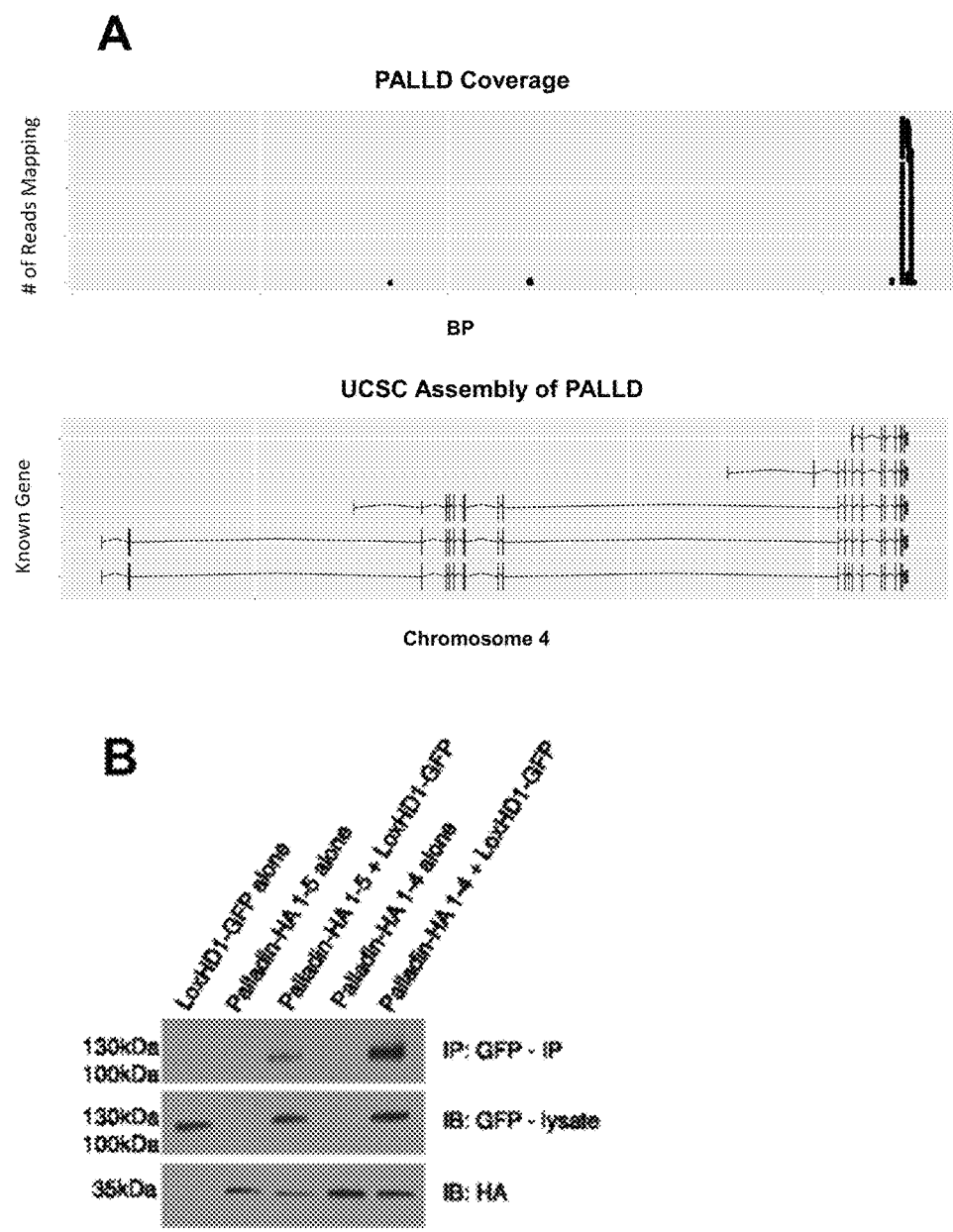

FIG. 6. Sequence analysis and validation for Loxd1-Palld. (A) Read mapping to exons for palladin (Palld) in Loxhd1-WT sample 6-2 (series 3) applying UCSC assembly. (B) Validation of palladin-Loxhd1 interaction in mammalian cells via co-IP of transiently expressed fusion proteins. Palladin-HA (in pcDNA3.1) and GFP1 tagged Loxhd1 containing 4 or 5 repeat domains were both expressed in HEK293 cells.

DETAILED DESCRIPTION OF THE INVENTION

In some aspects, the invention devised here constitutes a comprehensive screening and scoring scheme that applies next-generation sequencing to analyze the outcomes of Y2H, i.e. to identify and score selective prey proteins from tissue or organ-derived cDNA libraries that show physical interactions with designated bait proteins in individual screening assays. Replacing conventional sequencing with next-generation sequencing has two major implications. First, it will lead to a massively increased throughput, allowing for screening procedures that are up to 1,000-100,000-fold more efficient at reduced costs. Second, the larger amount of quantitative screening data enables a thorough statistical analysis of the results, with the important benefit that false positives can be systematically addressed and eliminated. This invention is therefore expected to enable Y2H screening that is vastly superior in terms of data output and cost to the alternatives currently available.

Addressing the need for an improved scoring of Y2H results, the devised global screening and scoring for next-generation sequencing of Y2H results allows also an increase in specificity. Hence, this overcomes a strong impediment for the successful application of high-throughput Y2H. The experimental steps follow essentially standard procedures for Y2H and can be applied to different Y2H and Y2H variant setup. However, the experimental procedures contain essential modifications at different steps to ensure an optimal and quantitative readout that allows for a maximum precision using quantitative statistics.

Figure 2:
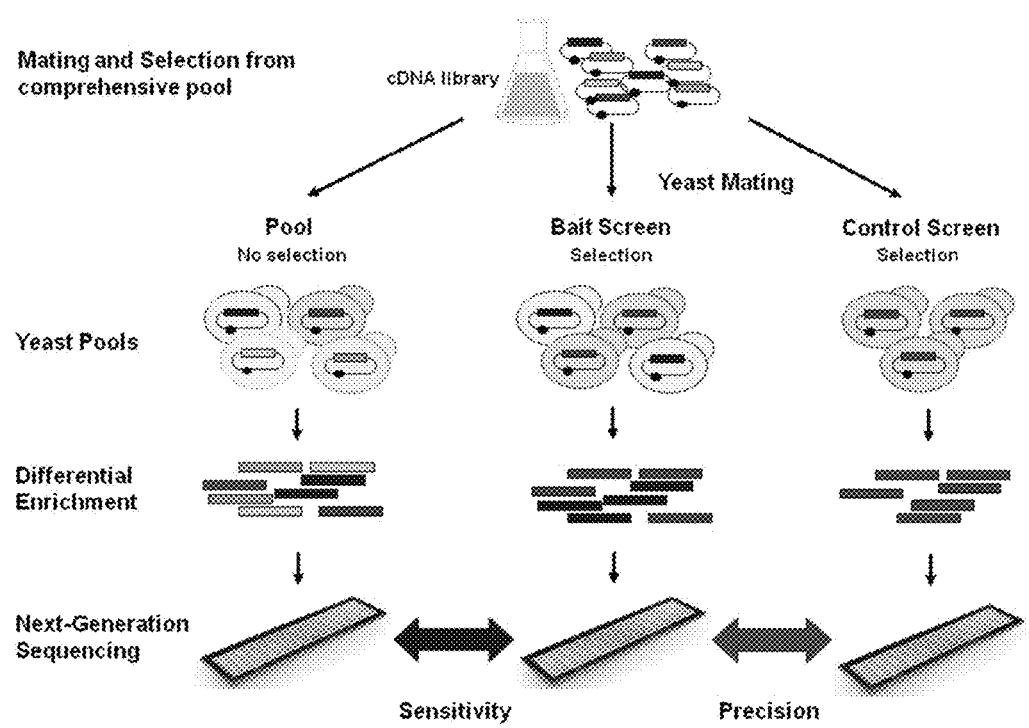
FIG. 2 shows the overall principle of a next-generation sequencing based Y2H approach. A pretransformed prey cDNA library in Matα mating strain background is mated with Mata Y2H strain containing select bait constructs (e.g. p53 oncoprotein) or empty vector control. The composition of the diploid pools that undergo Y2H selection (reporter activation) differs from the composition of the original pool. After plasmid extraction and PCR amplification of the prey inserts, the PCR products are prepared for DNA sequencing procedure (including the processing step shown in FIG. 3). The results from the bait screens are compared with the original starting samples. This 'pool comparison' (blue double-headed arrow) is showing enrichments of all interacting preys. With the 'vector comparison' (red double-headed arrow) bait-specific PPIs can be distinguished from unspecific PPIs

In an embodiment of the basic concept and implementation, we define here a global mating and selection scheme for the Y2H screens coupled to Illumina next-generation sequencing analysis (FIG. 2). cDNA libraries that are cloned into Y2H prey vectors are preset in aliquots were combined via transformation or yeast mating reactions with bait constructs. Yeast cells containing both bait and prey construct, as well as a set of reporter genes, are grown under selective conditions for reporter gene activation. Plasmid DNA is then isolated from selected and non-selected samples. Prey ORFs were amplified with a primer pair in the prey vector that flanks the recombination sites, yielding PCR products over the full range of expected sizes. The identification of the products, which is done using DNA microarrays in the basic version of the approach, or by next-generation sequencing systems, such as Illumina, or other NGS procedures. For any represented prey cDNA, the hybridization signals in the 'bait' screens, representing the preys selected in combination with a bait, are compared to two sets of 'control' samples: the original unselected pooled prey collection, which represents the background signal from a given library, and a control (vector or nonrepresentative bait protein) control, which is expected to display incorrect reporter gene activation in the absence of a functional bait.

In some aspects, the invention considers tissue- or organ derived cDNA libraries that were cloned into Y2H prey vectors as the source of the Y2H PPIs. By mating with individual Y2H bait and growth in selective medium, distinct cDNA populations will result depending on the bait for the Y2H screen and the length of the selective growth. It is important to note that, with this method, entire samples pools of are sequenced after an unbiased selection without the need to isolate individual clones. For optimal quantification of the selection process and, ultimately, the results from the screens, mated yeast pools are selected, starting with a defined and consistent number of cells and ending after a defined incubation time (e.g. 2-3 days) not exceeding 25 generations. Equivalent amount of cells from each individual selected (and unselected) pool are applied for DNA extraction. The defined processing steps for the experimental screening procedure, in conjunction with the generation of the quantitative sequencing readouts makes Y2H results amenable to statistical analysis.

It is important to note that our invention is not limited to any specific aspect of the Y2H screening system itself, such as designing and construction of reporter constructs, plasmid vectors or specific DNA elements for the generation of fusion constructs. The method of this invention provides a solution for a truly quantitative measurement of screening outcomes. Importantly, the systematic comparison to control experiments should greatly improve the confidence in the screening data since it allows a priori elimination of unspecific and obscure PPIs. This clearly distinguishes our approach from alternative procedures that aim primarily at very large screening throughput and sampling sensitivity. The proposed screening and scoring method is also not restricted to a particular Y2H platform and could, in principle, be applied as readout also to other screening methodologies.

Regarding the aforementioned framework for Y2H and a variant Y2H screening regarding completeness, assay and sampling sensitivity, and precision (specificity), our invention offers improvement in sampling sensitivity and precision. Both are made possible, in principle, by the massively increased capacity for sequencing the Y2H readouts. As a consequence, sequences can be analyzed efficiently when Y2H screens are executed at lowest level of stringency. Y2H screens at low stringency levels result often in hundreds to thousands of interactions that are tedious to interprete when applying conventional Y2H screening systems. In conventional Y2H screens, additional levels of stringencies are applied, i.e. the Y2H or modulation of the HIS3 reporter or activation of multiple reporter genes, with assumption to eliminate false positives. However, it is inevitable that genuine and true PPIs are lost when the stringency of the screening process is increased. When applying NGS Y2H, the generation of sequencing readouts is not a limiting factor and the application of additional levels of stringency therefore not as important. Hence, the massive increase of the sequencing power and, by inference, also the screening capacity allows a maximization of assay sampling sensitivity, i.e. every interaction that could be detected is very likely to be detected. In addition, the improved workflow also makes repeat screens using the same screening samples more feasible and practical, which makes it possible to get to a true saturation of the sampling.

In some aspects, concomitantly with increased throughput and sensitivity, the method and reagent kit disclosed herein deliver also increased precision. This is enabled by implementing a screening procedure, such as the one presented here that is comprehensive and quantitative at the same time. Since the readout (RNA sequencing) reflect the quantitative outcome of individual screens, Y2H interactions can be interpreted as continuous sets of numerical scores (see FIG. 4). This in turn allows the application of systematic controls and quantitative statistics to determine the probability that Y2H interactions are genuine and not caused by a spurious and unspecific PPIs or reporter activations. Specifically, by comparing prey cDNAs that were selected with a specific bait and those selected with control baits, promiscuous and non-specific PPIs can be identified and eliminated which increases the specificity or precision of the experimental outcome. Only prey cDNA clones that are significantly more enriched in the bait screen when compared to control screens can be considered to be bait-specific or genuine Y2H interactions. Prey cDNA clones that are selected not only in combination with a specific bait but also with no bait controls and irrelevant bait proteins can be ruled out as unspecific. Note that a bait protein can be defined if it has a totally different function or role than the specific bait protein. A no bait control is normally an empty bait vector construct, from which only the DBD is expressed. With the assumption that false positive prey activations can also be sampled up to completeness, the control screens should also be repeated to a maximum. These should ensure a complete sampling for potential false positives, in order to identify every prey in a cDNA library that has the potential to exhibit unspecific or spurious PPIs, for example with the DBD or endogenous yeast proteins.

The present disclosure also provides a special adaptation for the Y2H readouts for the Illumina or alternative next-generation sequencing system. When DNA-microarrays are applied for readouts, only simple labeling of the PCR products with biotin (Bio-Primer labeling system) before hybridization is required. When generating a library for the Illumina next-generation sequencing or another technology that applies fragmentation of the template into short fragments in order to obtain proper sequencing reads, a special preparation procedure is required (see FIG. 3). This step is performed prior to the fragmentation of the PCR products into smaller fragments and adaptor ligation. In principle, the preparation method can be considered as an addition and extension to the conventional RNA sequencing protocols. The goals for this procedure are (1) the removal of residual vector (PCR template) sequences, and (2) elimination of vector sequences flanking the cDNA inserts, encompassing the primer binding sites up to the cloning sites. Especially the flanking sequences could contribute to an excess of reads that are mostly noninformative but will occupy a large number of the available sequencing space, relative to the reads that are mappable to the Y2H prey inserts. The relative amount of these contaminating sequences depends on the distance between primer binding and cloning sites, but removal of these sequences should be considered nonetheless. Importantly, the efficient removal of contaminating flanking and priming sequences allows one to choose the primer binding sites at sequences that have the best biophysical properties and specificity in order to ensure an optimized PCR procedure.

Figure 3:
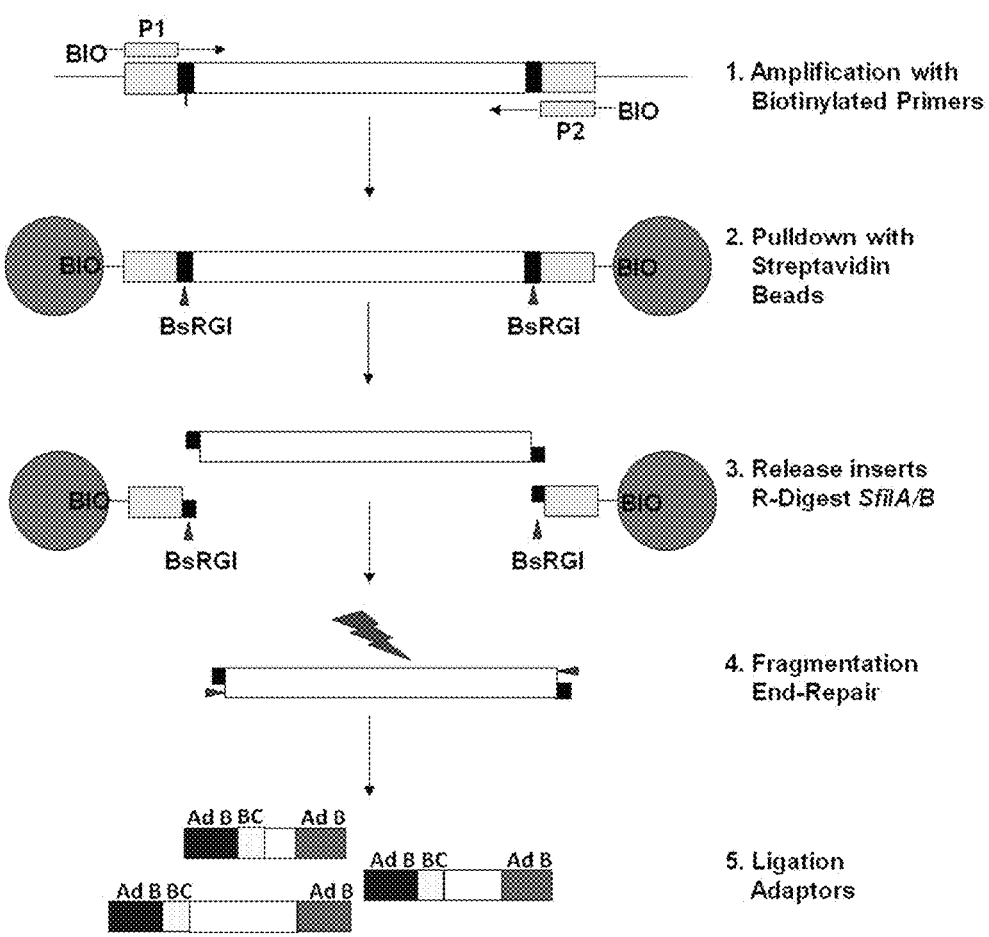
FIG. 3 shows a special purification step that is applied prior to the generation of a library for Y2H-NGS. (A) Scheme for preparation of PCR products. 1. Amplification of the prey cDNA pool using biotinylated primers (BIO). The biotin is attached to the 5' end of the primers via a TEG spacer arm to prevent steric hindrance for biotin binding. Primer binding sites (yellow) flank the cloning sites (black)
Figure 3:
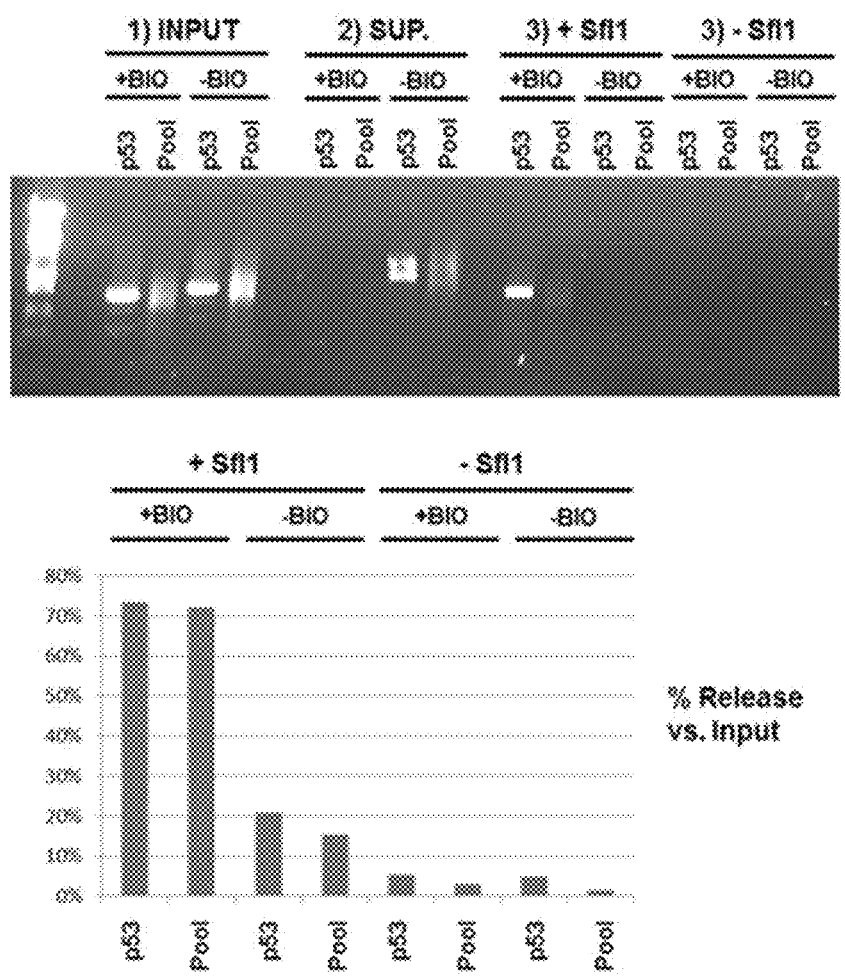
Figure 3:
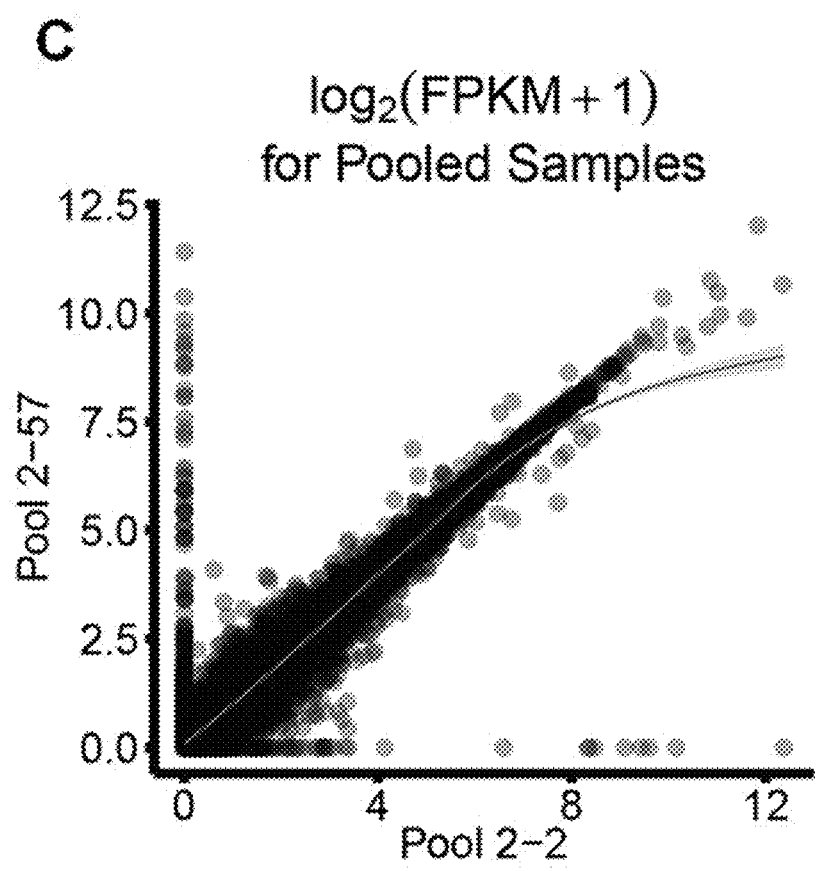

In another embodiment of the invention, the DNA sample preparation method for the HT-sequencing procedure starts with a special isolation and enrichment step, prior to the cDNA fragmentation, which will not only eliminate residual primers and template DNA, but also the sequences flanking the cDNA inserts up to the primer annealing site. FIG. 3 shows the concept (A) and the first proof-of-principle experiment (B). When the cDNA inserts are amplified, the primers annealing to the prey vector sequences are biotinylated at the respective 5' ends with a biotin modification (BIO-teg). For PCR prior to next-generation sequencing, the amount of cycles is kept small (range of 15-20 cycles), to avoid overamplification and the introduction of artifacts. The goal is a yield of 200-500 ng, which constitutes enough material for all subsequent preparations. The PCR products are cleaned up using the QIAGEN Buffer exchange or an equivalent protocol. In this step, residual BIO-teg primers and PCR solution are separated from the amplification product. The quality and quantity of the PCR product(s) is assessed by Bioanalyzer, Nanodrop or gel electrophoresis. (2) The BIO-teg labeled PCR products are incubated with streptavidin (Dynal), using a solution that entangles DNA molecules and favors access to the beads (Dynabeads® kilobase BINDER™ Kit or related chemical). Binding of the biotinylated PCR products is followed by 1-2 washes for the removal of nonbound DNA (vector template). (3) The bound DNA fragments are released from the Streptavidin beads by restriction digest. Conveniently, the same restriction enzyme can be applied that was used for the original cDNA cloning (e.g., SfiI for Clontech cDNAs). The digestion is performed like an ordinary restriction digestion and the released DNA fragments are further purified using QIAGEN Buffer exchange protocol. After these processing steps, the composition of the library can be assessed with a Bioanalyzer and quantitated. Comparing the DNA measurement with the respective input DNA, will allow determining the fraction of PCR products in will be lost in these processing steps. The subsequent steps will be performed according to standard protocols that are conventionally used for RNA sequencing, that include DNA fragmentation, ligation of adaptor primers and the actual sequencing procedure. In our proof-of-principle experiment (FIG. 3C), we found that this additional purification step does not introduce significant alterations into the composition of the purified products. Spearman correlation for the read mappings of several thousand gene fragments was 0.965, which is within the limit that is expected from technical replicates. Hence, selective loss of certain sequences is unlikely, apart from random effects.

The immobilization of the desired cDNA via biotin-streptavidin allows a very stringent and specific purification of contaminating and vector template DNA. While it is possible to do purification methods that rely solely on DNA binding or on DNA size fractionation, our purification strategy, exploiting biotin-streptavidin affinity allows maximum removal of contaminating sequences and is hence superior over potential alternative purifications. The method demonstrated in FIG. 3 is intended to ensure purity of the DNA of interest and sequestration of contaminating DNA. The biotin-streptavidin binding and release by restriction digest is executed under proper conditions that ensure that DNA fragment of all sizes and individual sequence compositions are properly released. The complete binding and the release of the complex pool of DNA fragments can be quantified by measurements with a Nanodrop or a Bioanalyzer.

After the selection process, a Y2H prey insert that is selected is expected to be identified with a large number of sequencing reads when compared with the original pool. Hence for a true Y2H selection a robust signal with yielding coverage up to several hundred-fold for the highly selected sequences. FIG. 4 shows an example, the readout from a Y2H screen that was generated with an Illumina GAII single read sequencing procedure with a p53 (control) fragment as a bait combined and a normalized human Matchmaker cDNA prey library. The integrated table (FIG. 4) shows the number of reads identified per geneID for the p53 bait screen occurrence of known positives (1: true, 0: false). The source for the known positives was a comprehensive collection of human PPIs (HIPPIE) (Schaefer, Fontaine et al. 2012). Only the 25 geneIDs within the top enrichment are shown. Normalized read numbers per prey GeneID are sorted according to read numbers. Since our screening procedure is comprehensive for the selection of a large number of PPI combinations, it allows, in principle, also the full exploitation of quantitative analysis tools that have been developed for transcriptome analysis and RNA sequencing. Hence, the approach presented here combines in a unique way the sequencing and identification of PPIs with a quantitative analysis that allows the identification of true positive and the elimination of false positive results by using various applicable statistical tools for known positive interactions (TOPORS, PIAS2, WDR48, COPS5) among the highest scoring ratios. While this illustration demonstrates the initial enrichment of sequences from Y2H interactions compared to the original unselected cDNA library, similar comparative sampling procedures could also be undertaken using other controls, i.e. control screens with empty vector and unrelated bait proteins. Statistical analysis can also be performed with other bioinformatics tools that address quantitative enrichments and comparisons for expression analysis and other purposes.

By applying multiplexing of the readouts using barcoded primers, further increase in throughput is possible for NGS-Y2H. Since typically only a few hundred ORFs or cDNAs are selected in a typical Y2H experiments, the capacity of the deep-sequencing readouts are greatly exceeding what is required for a single screen. Hence, indexed molecular barcodes can readily be applied for multiplexing and to achieve higher throughput and parallelization.

The NGS-Y2H method of the present disclosure was performed in a study of PPIs for the lipoxygenase homology domains 1 (Loxhd1) protein, which has a potential role in the mechanotransduction of sound (Grillet, Schwander et al. 2009). The samba mutation (LOXHD1-samba) causes hearing loss in mice. We screened for PPIs with a wild-type and mutant form (LOXHD1 and LOXHD1-samba.

Screens for Loxhd1-wild-type and Loxhd1-samba interactions were performed in 5 repeats, while T7 and Lam backgrounds for unspecific Y2H activation were also screened in 5 repeats, and 2 repeats were performed for the pool control. All readouts were generated with the MiSeq protocol, which could be completed in 3 days.

An optimized procedure was established for converting Y2H sample preparations to NGS-ready format using Illumina HiSeq, GaII and MiSeq, and also other platforms. After Y2H and plasmid DNA extraction from yeast, the complex mixture of selected prey cDNAs must be amplified before NGS sample prep. To avoid overamplification and the formation of PCR artifacts, the number of PCR cycles was optimized to ≤20 cycles by testing profiles of amplification products with a bioanalyzer. Plasmid extractions from yeast were accomplished using the Nextera protocol, which reliably allows preparation of a library from only a few nanograms of DNA.

In some experiments, pulling down biotinylated PCR products on avidin solid support was performed as an additional enrichment step before NGS. When comparing sequencing results from a cDNA pool prepared with or without the additional purification step, a modest increase in the percentage of reads that effectively mapped to human transcripts (from 85% to 92%, data not shown) were observed. Hence, the additional purification step may be optional in some cases.

The analysis of Y2H deep-sequencing data can be partitioned into primary, secondary, and tertiary analysis. Briefly, these steps filter raw reads, enrich statistically significant representations, and identify PPIs from overrepresented genes and pathways.

In the primary analysis, the raw reads from HiSeq and MiSeq were converted to fragments per kb per million reads (FKPM) using the Cufflinks-TopHat pipeline. In order to eliminate 3'UTR and other sequences, sequence counts that mapped to coding regions were filtered out.

In the secondary analysis, enrichments and statistical significances were calculated for the enriched bait-specific cDNAs over unspecific reporter activation (T7, Lam) and the original cDNA library (pool). Moreover, direct comparisons between PPIs for wild-type and mutant baits were made using one of the screen sets as a background. Three different statistics packages were applied to look for differential Y2H enrichments. EdgeR and DEseq are parametric approaches for differential expression testing that assume a negative binomial distribution (Robinson and Smyth 2008; Anders and Huber 2010; Robinson, McCarthy et al. 2010)(Robinson and Smyth 2008; Anders and Huber 2010; Robinson, McCarthy et al. 2010)(Robinson and Smyth 2008; Anders and Huber 2010; Robinson, McCarthy et al. 2010)(Robinson and Smyth 2008; Anders and Huber 2010; Robinson, McCarthy et al. 2010)(Robinson and Smyth 2008; Anders and Huber 2010; Robinson, McCarthy et al. 2010).

Finally, in the tertiary analysis, overrepresentation of pathways and gene ontology (GO) terms among the selected prey proteins was identified. The distribution of GO and pathway components within fold changes (FCs) was addressed with quantitative benchmarking and receiver operator characteristics (ROC). Such deep-sampling of Y2H data allows not only the identification of particular PPIs, but also the comparison of distinct PPI patterns (FIG. 5). Altered PPI patterns can predict functional consequences of gene mutations. The present NGS-Y2H method could therefore provide an efficient way to predict altered gene function; which impossible to make with conventional Y2H methods.

The data for PPIs shown in FIG. 5 were generated on the Illumina MiSeq. The focus was on potential associations of the Loxhd1 protein (FIG. 5). LOXHD1 encodes a highly conserved protein consisting entirely of PLAT (polycystin/lipoxygenase/alpha-toxin) domains. In mice, the samba mutation (Loxhd1-I1342N) substitutes a polar side chain for a hydrophobic side chain, thereby destabilizing the domain structure. This mutation leads to hearing loss due to perturbation of hair cell function and hair cell degeneration.

EdgeR-NB analysis from three comparisons (pool, T7, and Lam) revealed 44 and 57 enriched genes above the $70^{th}$ percentile cutoffs for Loxhd1-WT and mutant screens, and a similar set of high-scoring positives. However, differential PPIs between wild-type and mutant protein should be more relevant for the disease process under study (hearing disorders). Differential PPIs could have weaker binding and display less intense signals in the Y2H assay and therefore need to be addressed with a tailored data mining strategy. Here, data mining by QiSampler was used to address the distribution of geneIDs that are associated with the GO-term 'sensory perception of sound' in the EdgeR-NB FC scores for Loxhd1-WT bait screens (FIG. 5B). Precision-recall and ROC display enrich for genes with this term in the Loxhd1-WT screen. Quantitative enrichment of geneIDs associated with this GO-term can be seen for the Loxhd1-WT compared to the Loxhd1-samba screens.

Eight genes were identified with a role in the 'sensory perception of sound' among the enriched scores for Loxhd1-WT. Besides Loxhd1 itself (Samba), mutations in 3 other genes identified here are associated with hearing disorders. These include (1) wolframin (WFS1), the causative gene foe Wolfram syndrome 1, which includes loss of hearing among other phenotypes, (2) the unconventional myosin MYO6, and (3) ALMS1, causative for a ciliopathy that is characterized by different symptoms. Notably, it was also found for Loxhd1-WT enrichment of a partial clone for palladin (Palld), an actin filament-linked protein. These PPIs and their potential abrogation by the Samba mutation may underlie the hearing loss phenotype that is associated with LOXHD1.

The ability to use statistics and data mining, as in the example presented in FIG. 5 and Table 1, is one of the key benefits of the present NGS-Y2H method. Some genes can be addressed that are less significantly enriched, but may still be relevant for a process under study. Data mining for differential enrichment of pathways and GO terms among PPIs for wild-type versus mutant baits could predict the functional consequences of the mutation of interest. Hence, correlating PPI patterns with disease phenotypes may be a major application of the present NGS-Y2H method, providing rapid access to address the biological effects of mutations through altered PPI patterns.

TABLE 1

Enriched GO components for 'sensory perception of sound' and 'actin filament' in the EdgeR-NB FCs for the Loxhd1-WT screen set over background controls (Pool, T7, Lam) and loxhd1-samba. Genes with mutations that cause disease are indicated in cells shaded in yellow.

| Gene | perception of sound | actin filament | Pool | T7 | Lam | loxhd1-1342 |
|---|---|---|---|---|---|---|
| LOXHD1 | 1 | 0 | 5.68 | 1.50 | 8.99 | 9.91 |
| SNAI2 | 1 | 0 | 3.55 | 5.92 | 8.38 | 8.38 |
| CDKN1B | 1 | 0 | 7.70 | 2.28 | 3.16 | 6.86 |
| PALLD | 0 | 1 | 8.61 | 9.67 | 4.50 | 4.77 |
| ZNF354A | 1 | 0 | 6.93 | 9.43 | 9.05 | 4.48 |
| ALMS1 | 1 | 0 | 7.06 | 8.16 | 3.67 | 4.46 |
| MYO6 | 1 | 1 | 4.70 | 2.74 | 3.38 | 2.36 |
| RPL38 | 1 | 0 | 3.44 | 1.63 | 3.97 | 1.67 |
| WFS1 | 1 | 0 | 6.39 | 6.08 | 6.18 | −0.35 |

In this study, the emphasis was in detecting interactions between individual domains, and therefore partial protein fragments were selected as baits. Similarly, the specific validation assay was focused on the partial fragments retrieved from Y2H, rather than full-length proteins. Sequences from selected cDNA preys were amplified from the selected pools and cloned into mammalian expression vectors. Tagged prey fragments were then co-transformed into mammalian cell cultures with a construct encoding the original bait protein. A co-IP could then validate the Y2H interactions between bait and prey proteins.

FIG. 6 shows an example for the in-depth analysis and validation of the interaction of Loxhd1 bait protein with palladin. Close inspection of the Palld read mappings revealed that fragments at the 3' ends of the respective coding sequences were retrieved (FIG. 6A). After PCR amplification, the Palld fragment was cloned into a mammalian expression vector. Loxhd1-GFP fragments with 4 or 5 PLAT repeats were co-immunoprecipitated with Palld when both proteins were expressed (FIG. 6B).

The massive capacity and low cost of NGS-Y2H allow screening at a maximum sensitivity, such that a weak enrichment corresponding to a single clone can be detected in a larger overall population. Hence the present method can identify all potential positives, while conventional sequencing only allows the identification of the strongest and most enriched interactions. It is now affordable to generate extensive sets of experiments, even if only for purpose of background controls. Unspecific Y2H activation by a subset of prey cDNAs (sticky preys) often makes up a majority of all hits in a Y2H screen. Hence, without prior knowledge, conventional Y2H requires specificity tests of interactions, usually by isolation of cDNAs and retests with control strains. For NGS-Y2H the application of background controls and quantitative statistics allows the a priori exclusion of the unspecific interactions. Hence, when analyzing set of screens, cDNA enrichments are not only identified but also scored for specificity.

The present NGS-Y2H method eliminates the need for single colony isolation and also for stringent selection methods that require expensive reagents. This simplifies the screening procedure, reducing costs and allowing more screens to be run in parallel (10 and more). In principle, the labor and material cost for a Y2H screen (without cDNA library and sequencing), could be <$1,000.

Y2H results in NGS-Y2H can be interpreted as numerical scores over a log scale rather than as individual identifications. Quantitative comparisons between different screen sets allow data mining and predictions for gene function that cannot be made with the conventional Y2H approach. It is also important to realize that a compact set of quantitative data is far easier to handle than a large number of individual datasets.

While embodiments and applications of this disclosure have been shown and described, it would be apparent to those skilled in the art that many more modifications and improvements than mentioned above are possible without departing from the inventive concepts herein. The disclosure, therefore, is not to be restricted except in the spirit of the appended claims.

REFERENCES

Allison, D. B., X. Cui, et al. (2006). "Microarray data analysis: from disarray to consolidation and consensus." *Nat Rev Genet* 7(1): 55-65.

Alsford, S., D. J. Turner, et al. (2011). "High-throughput phenotyping using parallel sequencing of RNA interference targets in the African trypanosome." *Genome Res* 21(6): 915-924.

Anders, S. and W. Huber (2010). "Differential expression analysis for sequence count data." *Genome Biol* 11(10): R106.

Fields, S. and O. Song (1989). "A novel genetic system to detect protein-protein interactions." *Nature* 340(6230): 245-246.

Filichkin, S. A., H. D. Priest, et al. (2010). "Genome-wide mapping of alternative splicing in *Arabidopsis thaliana*." *Genome Res* 20(1): 45-58.

Fox, S., S. Filichkin, et al. (2009). "Applications of ultra-high-throughput sequencing." *Methods Mol Biol* 553: 79-108.

Giot, L., J. S. Bader, et al. (2003). "A protein interaction map of *Drosophila melanogaster*." *Science* 302(5651): 1727-1736.

Golemis, E. A., I. Serebriiskii, et al. (2009). "Interaction trap/two-hybrid system to identify interacting proteins." *Curr Protoc Protein Sci Chapter* 19: Unit 19 12.

Grillet, N., M. Schwander, et al. (2009). "Mutations in LOXHD1, an evolutionarily conserved stereociliary protein, disrupt hair cell function in mice and cause progressive hearing loss in humans." *Am J Hum Genet* 85(3): 328-337.

Hamdi, A. and P. Colas (2012). "Yeast two-hybrid methods and their applications in drug discovery." *Trends Pharmacol Sci* 33(2): 109-118.

Ito, T., T. Chiba, et al. (2001). "A comprehensive two-hybrid analysis to explore the yeast protein interactome." *Proc Natl Acad Sci USA* 98(8): 4569-4574.

Johnson, D. S., A. Mortazavi, et al. (2007). "Genome-wide mapping of in vivo protein-DNA interactions." *Science* 316(5830): 1497-1502.

LaCount, D. J., M. Vignali, et al. (2005). "A protein interaction network of the malaria parasite *Plasmodium falciparum*." *Nature* 438(7064): 103-107.

Lazarevic, V., K. Whiteson, et al. (2009). "Metagenomic study of the oral microbiota by Illumina high-throughput sequencing." *J Microbiol Methods* 79(3): 266-271.

Levin, J. Z., M. Yassour, et al. (2010). "Comprehensive comparative analysis of strand-specific RNA sequencing methods." *Nat Methods* 7(9): 709-715.

Lewis, J. D., J. Wan, et al. (2012). "Quantitative Interactor Screening with next-generation Sequencing (QIS-Seq) identifies *Arabidopsis thaliana* MLO2 as a target of the Pseudomonas syringae type III effector HopZ2." *BMC Genomics* 13: 8.

Marioni, J. C., C. E. Mason, et al. (2008). "RNA-seq: an assessment of technical reproducibility and comparison with gene expression arrays." *Genome Res* 18(9): 1509-1517.

Metzker, M. L. (2005). "Emerging technologies in DNA sequencing." *Genome Res* 15(12): 1767-1776.

Metzker, M. L. (2010). "Sequencing technologies—the next generation." *Nat Rev Genet* 11(1): 31-46.

Morozova, O. and M. A. Marra (2008). "Applications of next-generation sequencing technologies in functional genomics." *Genomics* 92(5): 255-264.

Paroush, Z., R. L. Finley, Jr., et al. (1994). "Groucho is required for *Drosophila neurogenesis*, segmentation, and sex determination and interacts directly with hairy-related bHLH proteins." *Cell* 79(5): 805-815.

Rajagopala, S. V., K. T. Hughes, et al. (2009). "Benchmarking yeast two-hybrid systems using the interactions of bacterial motility proteins." *Proteomics* 9(23): 5296-5302.

Ratushny, V. and E. Golemis (2008). "Resolving the network of cell signaling pathways using the evolving yeast two-hybrid system." *Biotechniques* 44(5): 655-662.

Robinson, M. D., D. J. McCarthy, et al. (2010). "edgeR: a Bioconductor package for differential expression analysis of digital gene expression data." *Bioinformatics* 26(1): 139-140.

Robinson, M. D. and G. K. Smyth (2008). "Small-sample estimation of negative binomial dispersion, with applications to SAGE data." *Biostatistics* 9(2): 321-332.

Rual, J. F., K. Venkatesan, et al. (2005). "Towards a proteome-scale map of the human protein-protein interaction network." *Nature* 437(7062): 1173-1178.

Schaefer, M. H., J. F. Fontaine, et al. (2012). "HIPPIE: Integrating protein interaction networks with experiment based quality scores." *PLoS One* 7(2): e31826.

Simonis, N., J. F. Rual, et al. (2009). "Empirically controlled mapping of the *Caenorhabditis elegans* protein-protein interactome network." *Nat Methods* 6(1): 47-54.

Stelzl, U., U. Worm, et al. (2005). "A human protein-protein interaction network: a resource for annotating the proteome." *Cell* 122(6): 957-968.

Uetz, P., L. Giot, et al. (2000). "A comprehensive analysis of protein-protein interactions in *Saccharomyces cerevisiae*." *Nature* 403(6770): 623-627.

Venkatesan, K., J. F. Rual, et al. (2009). "An empirical framework for binary interactome mapping." *Nat Methods* 6(1): 83-90.

Vidalain, P. O., M. Boxem, et al. (2004). "Increasing specificity in high-throughput yeast two-hybrid experiments." *Methods* 32(4): 363-370.

Walhout, A. J. and M. Vidal (2001). "High-throughput yeast two-hybrid assays for large-scale protein interaction mapping." *Methods* 24(3): 297-306.

Yu, H., P. Braun, et al. (2008). "High-quality binary protein interaction map of the yeast interactome network." *Science* 322(5898): 104-110.

Zhang, L. Q., D. Cheranova, et al. (2012). "RNA-seq reveals novel transcriptome of genes and their isoforms in human pulmonary microvascular endothelial cells treated with thrombin." *PLoS One* 7(2): e31229.

What is claimed is:

1. A method for determining the DNA sequences of prey proteins that interact with bait protein, comprising:
   (1) conducting a bait screen comprising the steps of:
      (a) introducing a library of Y2H prey vectors into a Y2H host strain to produce a library of hybrid Y2H cells, wherein each of said Y2H prey vectors includes prey fusion construct for expressing a prey fusion protein, wherein said Y2H host strain includes assay bait fusion construct, and wherein said hybrid Y2H cells include reporter gene construct;
      (b) growing said hybrid Y2H cells in a selecting condition for a defined time or for a defined cell growth, wherein cell growth correlates to expression of said reporter gene construct;
      (c) PCR amplifying prey open reading frame in the prey fusion construct from said library of hybrid Y2H cells using a flanking set of specific primers, wherein amplification is done under controlled conditions to avoid generation of artifacts and erroneous PCR products;
      (d) purifying pool of PCR amplified prey ORFs; and
      (e) analyzing pool of purified PCR amplified prey ORFs using a high throughput DNA sequencing method that reads DNA sequences and gives quantitative information of composition of said pool of purified PCR amplified prey ORFs,
      wherein all outcomes from said bait screen are from sequencing of the single pool of purified PCR amplified prey ORFs;
   (2) conducting one or more control screens that are parallel to said bait screen but with one or more differences selected from the group consisting of:
      (a) in lieu of step (1)(a): introducing a library of Y2H prey vectors into a Y2H host strain to produce a library of hybrid Y2H cells, wherein each of said Y2H prey vectors includes prey fusion construct for expressing a prey fusion protein, wherein said Y2H host strain includes control bait fusion construct, and wherein said hybrid Y2H cells include reporter gene construct;
      (b) in lieu of step (1)(a): introducing a library of Y2H prey vectors into a Y2H host strain to produce a library of hybrid Y2H cells, wherein each of said Y2H prey vectors includes prey fusion construct for expressing a prey fusion protein, wherein said Y2H host strain does not include any bait fusion construct, and wherein said hybrid Y2H cells include reporter gene construct; and
      (c) in lieu of step (1)(b): growing said hybrid Y2H cells, in a non-selecting condition, for a defined time or for a defined cell growth; and
   (3) applying quantitative statistics using computer to determine bait specific positive results.

2. The method of claim 1, wherein multiples of bait screens and control screens are conducted to obtain discrete sets of scores, and computer operated quantitative statistics is applied to determine bait specific positive results, and to assess relationship between bait mutation and protein-protein interaction.

3. The method of claim 1, wherein: among each pair of the flanking set of specific primers, at least one of them includes at least one affinity tag.

4. The method of claim 3, wherein said affinity tag is selected from the group consisting of biotin, glutathione, His, Flag, thiol, amino, azido, and acetylene.

5. The method of claim 4, wherein said affinity tag is biotin.

6. The method of claim 5, comprising:
   (1) incubating biotinylated PCR product mixture with streptavidin coated solid support,
   (2) washing to remove unbound DNA and other components in PCR reaction mixture, and
   (3) treating said streptavidin coated solid support with restriction enzyme to release immobilized prey cDNA inserts, and
   wherein said streptavidin coated solid support is magnetic bead.

7. The method of claim 6, wherein said restriction enzyme is a restriction enzyme that recognizes and cuts at restriction sites used for cloning said prey cDNA construct.

* * * * *